United States Patent
Gazzola et al.

(10) Patent No.: US 10,416,065 B2
(45) Date of Patent: Sep. 17, 2019

(54) DEVICE FOR REAL TIME ANALYSIS OF PARTICLES SUSPENDED IN A FLUID AND METHOD FOR THE ANALYSIS OF SAID PARTICLES

(71) Applicant: CELLDYNAMICS I.S.R.L., Imola (IT)

(72) Inventors: Daniele Gazzola, Bologna (IT); Simone Pasqua, Spilamberto (IT); Emanuele Centurioni, Bologna (IT)

(73) Assignee: CELLDYNAMICS I.S.R.L., Imola (IT)

( * ) Notice: Subject to any disclaimer, the term of this patent is extended or adjusted under 35 U.S.C. 154(b) by 235 days.

(21) Appl. No.: 15/535,830

(22) PCT Filed: Dec. 16, 2015

(86) PCT No.: PCT/IB2015/059670
§ 371 (c)(1),
(2) Date: Jun. 14, 2017

(87) PCT Pub. No.: WO2016/098011
PCT Pub. Date: Jun. 23, 2016

(65) Prior Publication Data
US 2017/0370818 A1    Dec. 28, 2017

(30) Foreign Application Priority Data
Dec. 16, 2014   (IT) ............... VI2014A0313

(51) Int. Cl.
*G01N 15/10* (2006.01)
*B01L 3/00* (2006.01)
*G01N 15/14* (2006.01)

(52) U.S. Cl.
CPC ........ *G01N 15/10* (2013.01); *B01L 3/502761* (2013.01); *B01L 2200/0663* (2013.01);
(Continued)

(58) Field of Classification Search
None
See application file for complete search history.

(56) References Cited

U.S. PATENT DOCUMENTS

| 2004/0072278 A1 | 4/2004 | Chou et al. .............. 435/29 |
| 2004/0096977 A1 | 5/2004 | Rakestraw et al. ......... 436/63 |

(Continued)

FOREIGN PATENT DOCUMENTS

| CN | 102472739 | 5/2012 |
| CN | 103282123 | 9/2013 |
| WO | WO-2008068680 A2 * | 6/2008 ........... B03C 1/282 |

OTHER PUBLICATIONS

Italian Search Report from corresponding Italian Application VI20140313 dated Aug. 27, 2015, 2 pages.
(Continued)

*Primary Examiner* — Kathryn Wright
(74) *Attorney, Agent, or Firm* — Fattibene and Fattibene LLC; Paul A. Fattibene (57) ABSTRACT

The present invention refers to a device for the analysis of a particle comprising an analysis chamber adapted to contain a positioning fluid. A parameter of the particle suspended in the positioning fluid is detected by means of a detection and control unit. A positioning unit, during a particle analysis operation, is activated and deactivated on the basis of the detected parameter of the particle. The detection and control unit can activate the at least one positioning unit so as to generate a temporary positioning flow in the positioning fluid, such that said temporary positioning flow acts directly on the particle and drives the position of the particle so as to move it into a predefined position in the analysis chamber. The detection and control unit can also deactivate the at least one positioning unit when the particle to be analyzed is in the predefined position, such that the positioning fluid is at rest.

22 Claims, 6 Drawing Sheets (52) U.S. Cl.
CPC .............. *B01L 2400/0445* (2013.01); *B01L 2400/0481* (2013.01); *B01L 2400/0487* (2013.01); *G01N 2015/1006* (2013.01); *G01N 2015/1075* (2013.01); *G01N 2015/1415* (2013.01)

(56) References Cited

U.S. PATENT DOCUMENTS

| | | | |
|---|---|---|---|
| 2005/0074869 A1 | 4/2005 | Yoshida et al. | 435/287.1 |
| 2005/0112606 A1 | 5/2005 | Fuchs et al. | 435/6 |
| 2006/0005634 A1 | 1/2006 | Schroeder et al. | 73/861 |
| 2010/0006441 A1 | 1/2010 | Renaud et al. | 204/643 |
| 2011/0189701 A1 | 8/2011 | Kim | 435/7.9 |
| 2011/0263030 A1 | 10/2011 | Kim | 436/45 |
| 2014/0087412 A1 | 3/2014 | Fouras et al. | 435/29 |
| 2018/0141045 A1 | 5/2018 | Verrant et al. | B01L 3/502707 |

OTHER PUBLICATIONS

Chinese Office Action dated Apr. 28, 2019 in corresponding Chinese patent application No. 201580069234.4, 8 pages.

* cited by examiner

Figure 1
(state of the art)

Figure 2
(state of the art)

DEVICE FOR REAL TIME ANALYSIS OF PARTICLES SUSPENDED IN A FLUID AND METHOD FOR THE ANALYSIS OF SAID PARTICLES

The present invention regards a device for the analysis of a particle immersed in a fluid. In particular, the present invention refers to a device which includes a positioning unit for controlling the position of the particle to be analyzed in an analysis chamber. The control of the position of the particle to be analyzed occurs by means of the driving of the particle to be analyzed by flows selectively generated in the fluid in the analysis chamber. The present invention also refers to a method for analyzing a particle immersed in a fluid.

STATE OF THE ART

Devices and methods for executing analyses of biological material, and in particular single cells by means of the use of microfluidic systems, are known from the state of the art. Specifically, microfluidic systems for the cell analysis or analysis of biological material allow the introduction of the material to be analyzed in an analysis chamber and trap the material to be analyzed in the analysis chamber. For the purpose of the analysis, the cell or the material to be analyzed must remain in a predefined position, which can be the focal point of an optical analysis system, for a predetermined time period.

Various solutions are known from the state of the art, which allow trapping a cell or a particle in a precise position of an analysis chamber or of a microfluidic channel. Specifically, microfluidic analysis systems are known in which the position of the particle to be analyzed is controlled by means of optical traps. In such system, a focused laser beam is used for transferring a momentum to the particle so as to trap it in the direction of the laser beam and manipulate it. Alternatively, solutions are known which provide for the control of the position of the particle to be analyzed by means of dielectrophoretic traps. In such systems, the position of a dielectric particle can be controlled through the generation of a variable, non-uniform electric field. Magnetic traps can instead be used for trapping magnetized particles. Other solutions known from the state of the art provide for the use of mechanical traps that allow blocking the particle to be analyzed in a precise point, for example by means of adhesion.

Such solutions have the disadvantage that the used systems require rather complicated devices for trapping the particle to be analyzed, such as lasers, configurations of quadrupoles or electromagnetic systems. The design and economic effort increases if it is desired to control the position of the particle to be analyzed not along only one direction but in the three spatial dimensions. Another disadvantage of such solutions is given by the fact that the above-described traps subject the particle to be analyzed to stresses of mechanical, chemical and/or thermal type. A further disadvantage of such solutions is given by the fact that the fluids in which the cells are cultivated and analyzed must respect stringent characteristics for the operation of the device, e.g. lack of floating corpuscles for optical traps, or a low electrical conductivity in the case of dielectrophoretic traps. If the particle to be analyzed is a cell or biological material, such stresses can damage or compromise the cell itself, altering or even ruining the analysis. In addition, the analysis devices which use mechanical traps, in addition to the above-listed disadvantages, also do not allow an easy repositioning of the previously-trapped particle, if such particle must be moved or removed from the device.

Other systems that are known from the state of the art provide for devices that allow trapping the particle to be analyzed by means of fluid-dynamic traps. Such microfluidic systems comprise a main transport channel, in which particles to be analyzed are transported in a fluid, and a plurality of lateral channels. Each of the lateral channels has size such to allow trapping the cells via suction in case a part of the fluid that flows in the main channel is sucked into said channel. Even if such system allows trapping the particle to be analyzed in a well-defined position of the instrument, devices based on fluid-dynamic traps do not allow flexibly controlling the position of the particle to be analyzed in an analysis chamber: the particle can be trapped and then maintain a predefined position only at the lateral channels. A precise regulation of the position of the particle to be analyzed in any point of the analysis chamber is not possible in such systems. Once sucked into a secondary channel, moreover, the particle to be analyzed can adhere to the walls of the secondary channel, subjecting the particle to be analyzed to possible mechanical stresses. In addition, if the particle to be analyzed is a cell, the adhesion of the cell to the walls of the channel can induce changes in the cell, thus distorting the results of the analysis.

Other devices for the observation and/or analysis of particles allow trapping the particle to be analyzed by means of fluid-dynamic traps by introducing continuous and opposing flows of fluid in the analysis chamber, so as to generate in the analysis chamber a point of equilibrium or stagnation point in which the fluid has zero velocity. Examples of systems that exploit such principle can be found in US 2014/0087412 A1 and US 2006/0005634 A1.

Figure 1:
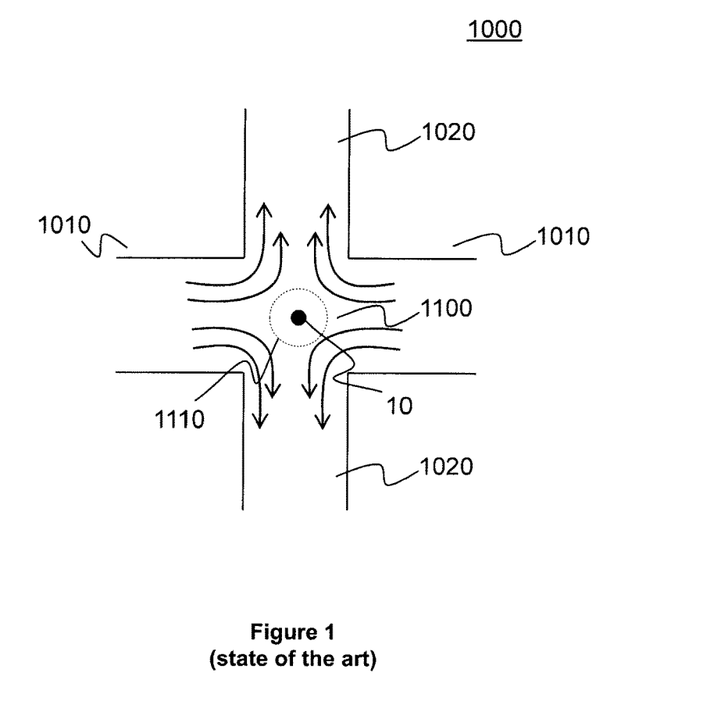
FIG. 1 schematically shows a detail of a first microfluidic device for the analysis of a particle, known from the state of the art.

In addition, an example of a fluid-dynamic system that exploits such principle is illustrated in FIG. 1. The device for trapping the particle to be analyzed comprises an analysis chamber 1100 in fluidic communication with fluid introduction channels 1010 and drain channels 1020. A particle to be analyzed 10 is trapped inside a stagnation zone 1110, in which the velocity of the fluid in which the particle is immersed is zero. The particle to be analyzed 10 is moved or held in position through the stagnation zone 1110, which can be moved by controlling the flow through the introduction channels.

Figure 2:
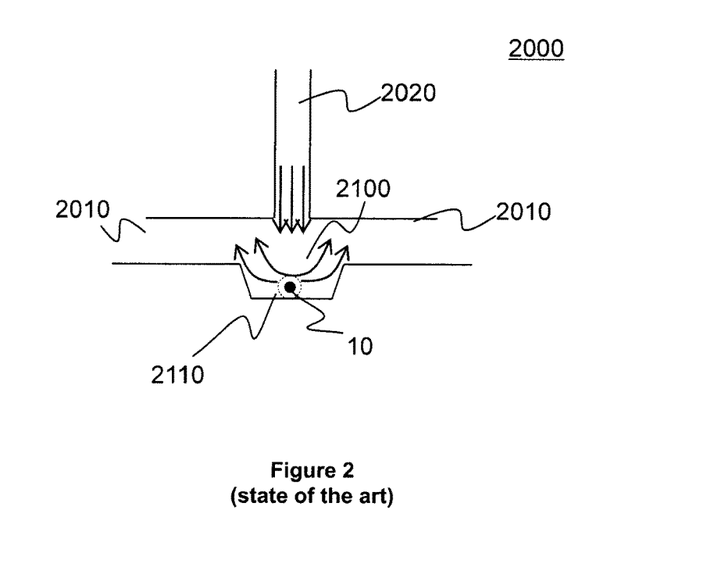
FIG. 2 schematically shows a detail of a second microfluidic device for the analysis of a particle, known from the state of the art.

FIG. 2 shows an alternative analysis device, known from the state of the art. The fluid is introduced, through an introduction channel 2020, into a well 2100 with tilted lateral walls. The particle 10 is thus thrust towards the bottom of the well 2100 while the fluid flows outside the through lateral expulsion channels 2010. The fluid introduced through the channel 2020 is divided on the bottom of the well 2100 and flows on the tilted walls outside said well so as to generate a stagnation point 2110 on the bottom of the well. The particle to be analyzed 10 remains trapped on the bottom of the well in the stagnation point 2110 until the fluid is introduced in the well 2100 through the channel 2010.

The technology described above with reference to FIGS. 1 and 2 requires continuous introduction of at least one flow inside the analysis chamber and a geometry of the analysis chamber such to be able to generate a stagnation zone. Technologies that are based on the creation of stagnation zones induce, in the analysis chamber or in the well, continuous flows that have flow rate and direction such to generate, inside the analysis chamber, a region of fluid in which the flow is stationary, where the particle remains trapped. In general, in such systems, continuous flows are present in the fluid of the analysis chamber except in the zone of the analysis chamber where the flows meet. In other words, a flow gradient is introduced in the analysis chamber such to create a minimum flow zone where the particle is trapped.

Such devices are unable to directly control the flow of fluid acting on the particle to be analyzed, which is not directly moved (driven) through the action of flow thereon but indirectly moved by means of the movement of a minimum flow zone (stagnation zone): a variation of the flow rate of one of the continuous flows induced in the analysis chamber will produce an instability of the stagnation zone, which does not necessarily cause the maintenance in motion of the particle inside the trap. Such solution, which provides for the trapping of the particle by means of continuous fluid flows, on one hand involves the use of large quantities of fluid, often costly in the case of biological analyses, and on the other hand renders the position control system quite complex and costly.

In all the technological solutions for the three-dimensional control of the position of particles to be analyzed by means of traps, and described above, the actuation component is part of the system and must be considered an integral part of the technological solution. In particular, in addition to the specific actuators, e.g. electrodes for dielectrophoretic traps, or laser systems for optical traps, such systems include valves and pumps dedicated for the selection and generation of flows. The pumps commonly used for creating flows in the above-described devices have characteristics that render them suitable for the positioning of a particle by means of the above-described technical expedients. Such pumps are commonly sized so as to generate high linear velocities in the channels connected with the region where the analysis of the particle occurs. Such velocities are on the order of magnitude of one hundred micrometers per second or higher.

The present invention sets the objective of resolving the above-listed problems. Specifically, the object of the present invention is to develop a technique that allows effectively controlling the position of a particle immersed in a fluid in an analysis chamber in a manner so as to prevent subjecting the particle to be analyzed to stress, in particular mechanical, chemical, biochemical, and biological stresses. In addition, the object of the present invention is to develop a device and a method that allow a precise control of the position of the particle to be analyzed in the three spatial dimensions, which is simple to use and which allows reducing the costs of use.

SUMMARY OF THE INVENTION

The object of the present invention is resolved by the independent claims. Advantageous embodiments of the present invention are the object of the dependent claims.

In particular, the invention refers to a device for the analysis of a particle and in particular suitable for being used in order to analyze biological material such as cells or the like, or non-biological material such as polymer microparticles. The device comprises an analysis chamber adapted to contain a positioning fluid. A parameter of the particle suspended in the positioning fluid is detected by means of detection and control unit. The device also comprises at least one positioning unit adapted, during a particle analysis operation, to be activated and deactivated on the basis of the detected parameter of the particle. In particular, the detection and control unit is adapted to activate the at least one positioning unit so as to generate a temporary positioning flow in the positioning fluid in a manner such that said temporary positioning flow acts directly on the particle and drives or controls the position of the particle so as to move it into a predefined position in the analysis chamber. The detection and control unit is also adapted to deactivate the at least one positioning unit when the particle to be analyzed is in the predefined position, such that the positioning fluid is at rest.

In other words the positioning unit is adapted to induce, in the positioning fluid, a flow (termed positioning flow hereinbelow) that causes a movement of the movement fluid portion at the detected position of the particle to be analyzed in a specific direction and with a specific velocity. Such movement of the portion of the positioning fluid, in particular the direction and the velocity of the portion of the positioning fluid, is determined on the basis of detected parameters of the particle to be analyzed.

The control of the position of the particle to be analyzed occurs via driving and not via trapping. Indeed there is no position inside the analysis chamber that can be defined 'trap', i.e. there is no light intensity end (as in the case of optical traps), no electromagnetic field intensity end (as in the case of dielectrophoretic traps), or no point with locally zero flow (as in the case of stagnation point traps) which generate a trap for the particle to be analyzed. By 'end' it is intended a relative maximum or minimum point.

Due to the system of the present invention, it is possible to directly operate on the position of the cell, avoiding damage from stress and the typical instability of the traps. In particular, the pressure gradients in the analysis chamber and the driving by friction have negligible effects with respect to the normal behavior of the particle in suspension in the fluid.

By means of the analysis device of the present invention, it is also possible to maintain a particle to be analyzed—such as a cell, a molecule or biological material in general—substantially stopped at a precise point in the three-dimensional space, such as the focal point of an optical device, or the operating region of a sensor or actuator, including but not limited to the following: electrochemical microsensors, optical or electrochemical biosensors, microscope tips with atomic force, cantilevers, needles, microtubes, nanotubes. In fact the generated flows can be used for counter-balancing the forces that act on the particle at rest of the analysis chamber, such as the gravitational force, Archimede's thrust, and/or random motions, e.g. convective motions of the fluid in which the particle to be analyzed is immersed. In addition, the desired position can also be defined as a function of the distance with respect to other floating objects in the analysis chamber, such as other cells, drug carriers, microspheres. Otherwise the generated flows can be used for inducing the particle to be analyzed to follow a predefined path in the three-dimensional space.

The invention also refers to a method for analyzing a particle, in particular biological material, such as cells and the like or non-biological material such as polymer microspheres. Said method comprises the introduction of the particle to be analyzed in an analysis chamber containing a positioning fluid. A parameter of the particle in the analysis chamber, where the particle to be analyzed is in suspension in the positioning fluid, is then detected through a position detection device, such as a detection and control unit. The method also comprises the generation, during a particle analysis operation, of a temporary positioning flow in the positioning fluid through the activation of at least one positioning unit, where said temporary positioning flow acts directly on the particle and drives the particle into a predefined position in the analysis chamber. The method also comprises the deactivation, during a particle analysis operation, of the at least one positioning unit when the particle to be analyzed is in the predefined position, such that the positioning fluid is at rest.

According to one aspect of the invention, the temporary positioning flow is generated without mechanical or electrical elements coming into direct contact with the positioning fluid.

BRIEF DESCRIPTION OF THE FIGURES

The enclosed figures are incorporated in the description and form a part thereof for the purpose of illustrating different embodiments of the present invention. The aforesaid figures together with the description serve to explain the principles of the invention. The figures are provided for the sole purpose of illustrating preferred and alternative examples of how the invention can be achieved and used, and are not to be interpreted for limiting the invention to only the illustrated and described embodiments. Additional characteristics and advantages will be apparent from the following more detailed description of the different embodiments of the invention, as illustrated in the enclosed figures, in which equivalent numbers refer to equivalent elements.

DETAILED DESCRIPTION OF THE FIGURES

The following paragraphs describe different exemplifying embodiments of the present invention. By way of example and in order to facilitate comprehension, the embodiments will be described with reference to the analysis of biological material such as cells or cell agglomerates, indicated hereinbelow with the generic term of particles. It is in any case understood that the device and the method of the present invention can also be used for controlling the position of particles of non-biological nature in a fluid through the selective generation of positioning flows. In particular, the solutions described with reference to the exemplifying embodiments described below can also be used in order to analyze particles different from cells or cell agglomerates.

Consequently, the term "particle", used in the context of the present invention for indicating cells, cell agglomerates or in general biological material, can also be used for indicating different objects, such as microparticles and nanoparticles, residue particulate of industrial production processes, atmospheric dust in suspension, pollen, oil drops in aqueous suspension, air bubbles in liquids.

The term "fluid" is used in the exemplifying embodiments of the present invention for indicating a generic cell culture terrain. The man skilled in the art will however clearly understand that the term fluid must be interpreted in its most general meaning, and hence comprises not only liquids but also gases. In particular, in accordance with the design needs and the particles to be analyzed, the man skilled in the art will clearly understand that gases or liquids of another nature can also be used in the analysis chamber of the device of the present invention, in order to support the particle and to control the position thereof.

With the term "driving" it is hereinbelow intended a transport mechanism for the particle to be analyzed that exploits the friction between a one-way flow generated in the analysis chamber and the particle to be analyzed. The driving mechanism contrasts with trapping mechanisms based on the creation of a stagnation zone since in the latter, the flow that positions the particle has a saddle profile, i.e. it is not one-way.

The term "one-way flow" used in this context is to be intended as the outcome of a plurality of flows induced in the analysis chamber around the particle to be analyzed.

The term "analysis chamber" is used for indicating a well adapted to contain the fluid in which the particle to be analyzed can float, and into which one or more channels used for generating the positioning flows can converge. In particular, with the term analysis chamber, it has to be intended not only the space in the immediate proximity to the particle to be analyzed but rather the entire well.

In the context of the present invention controlling the position of the particle to be analyzed must be intended in its widest meaning and comprises both the maintenance of the particle in a predefined position in the analysis chamber and the movement of the particle to be analyzed, which is in suspension in a fluid, inside the analysis chamber. Other possibilities for controlling the position of the particle will be clearer in the following description.

The present invention is based on the observation that microfluidic devices known from the state of the art and used for executing cell analysis may use invasive techniques for capturing the particle to be analyzed and controlling the position thereof by means of traps, or they do not allow an easy and precise control of the position of the particle in the analysis chamber. Specifically devices based on methods of trapping and mechanical, optical, electromagnetic or dielectrophoretic positioning subject the cell to be analyzed a stresses which in some cases risk modifying the structure itself of the particle to be analyzed. On the other hand, analysis devices based on fluid-dynamic techniques such as techniques that exploit the creation of a stagnation point, while not being invasive, require a control system which can only be attained today with technologies so complex and costly that they preclude market diffusion.

One object of the present invention is to provide a device for analyzing a particle immersed in a fluid that is capable of maintaining a particle, such as a cell or a set of cells, in a predefined position in an analysis cell. The predefined position in which the particle to be analyzed is maintained can for example be the focal point of an optical analysis instrument. Alternatively, the predefined position can be the position in which the analysis or the stimulation of the particle is carried out. Specifically, the device according to the present invention allows controlling the position of the particle to be analyzed.

The idea underlying the present invention is that of using the local flows, induced in the positioning fluid in the analysis chamber, which result, in one point of the analysis chamber corresponding to the current position of the particle, in a one-way flow that drives the particle to be analyzed into a predefined position. Such local flows induced in the positioning fluid in the analysis chamber directly act on the spatial position of the particle, moving it by driving (friction forces); they do not act by means of the formation of traps that attract the particle, as described above in the analysis devices that exploit the technology of the stagnation zone. In addition, during the positioning operations, the local flow at the position of the particle to be analyzed is non-zero, and the velocity of such flow is directly transmitted to the particle, adding to the movement of the particle inside the fluid.

The relative movement with respect to the fluid of the particle to be analyzed could for example be a random due to external agents, such as the force of gravity, Archimede's thrust, or local convective motion within the positioning fluid. Alternatively, the relative movement with respect to the fluid of the particle to be analyzed can be a drift movement due to the initial velocity that the particle to be analyzed acquired during system initialization. In other words, in the analysis device of the present invention, the particle to be analyzed is driven through the use of local flows that are generated based on one or more parameters of the system and which generate the desired movement in real time, even counterbalancing the relative movement with respect to the fluid of the particle to be analyzed.

The control of the position of the particle occurs according to the present invention by means of the selective generation of a positioning flow directly at the particle to be analyzed, thus preventing the use of mechanical or electrical means for the positioning of the particle to be analyzed, as will be described hereinbelow. In such a manner, it is possible to prevent subjecting the particle to be analyzed to stresses, in particular mechanical, chemical, biochemical, and biological stresses. Simultaneously, the device and the method of the present invention allow precisely controlling the position of the particle to be analyzed.

Figure 3:
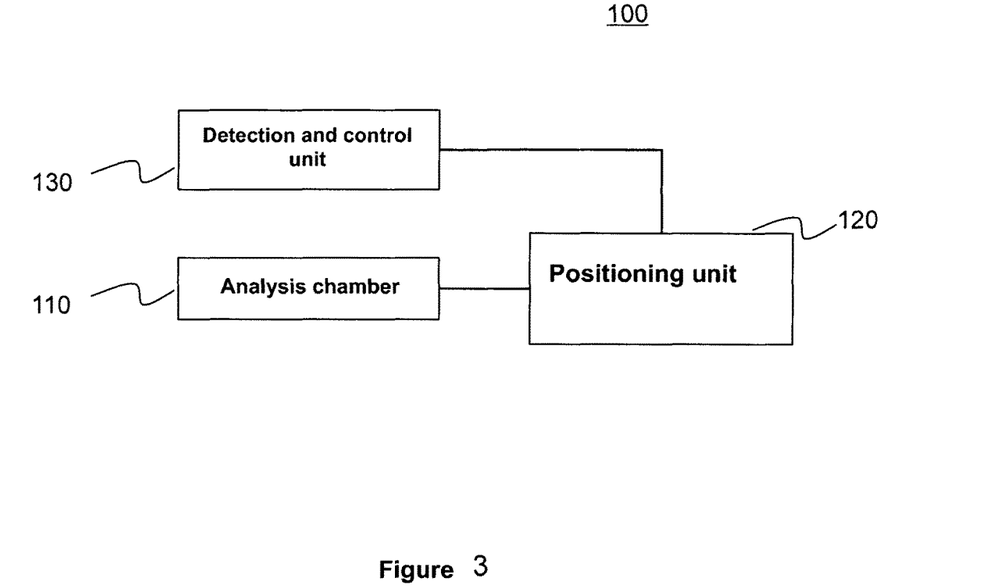
FIG. 3 is a schematic representation of an analysis device according to one embodiment of the present invention.

FIG. 3 is a schematic representation of an analysis device 100 according to the present invention. The device 100 comprises an analysis chamber 110 adapted to contain a positioning fluid. One parameter, e.g. the position of the particle suspended in the positioning fluid, or the position and the velocity of the particle to be analyzed in the analysis chamber, is detected by means of a detection and control unit 130. In the analysis chamber 110, the positioning fluid is essentially at rest. In other words, in the fluid, only the positioning flow is present, with much lower flow rate than the flows conventionally induced in comparable microfluidic systems, in accordance with the definition of the "driving" mechanism given above. In other words, in the fluid at rest, flows are not present that are constant and permanent or induced by pumps in fluidic connection with the analysis chamber and adapted to generate a stagnation zone in the analysis chamber 110.

The device 100 also comprises at least one positioning unit 120 adapted to control a position of the particle in the positioning fluid. Such control of the position occurs through the generation, in the positioning fluid, of a positioning flow on the basis of the detected parameter of the particle, which drives the particle into the desired position. Specifically the positioning unit, during a particle analysis operation, can be activated and deactivated on the basis of the detected parameter of the particle, as explained hereinbelow.

The detection and control unit 130, after having detected one or more current parameters of the particle in suspension in the analysis chamber 110, activates the at least one positioning unit 120 so as to generate a temporary positioning flow in the positioning fluid. Said temporary positioning flow acts directly on the particle and drives the particle into a predefined position in the analysis chamber.

When the particle to be analyzed 10 is in the predefined position, e.g. the focal point of an optical analysis device, the detection and control unit 130 can deactivate the at least one positioning unit 120 such that the positioning fluid is at rest.

During a particle positioning operation, the velocity of the positioning flow at the particle is non-zero. In other words the positioning unit 120 is adapted to induce, in the positioning fluid, a flow (termed positioning flow) that causes a movement of the positioning fluid portion at the detected position of the particle to be analyzed in a specific direction and with a specific velocity. Such movement of the portion of the positioning fluid, in particular the direction and the velocity of the portion of the positioning fluid, is determined based on parameters such as the detected position of the particle to be analyzed.

The at least one positioning unit 120 generates the positioning flow, which can assume any spatial direction and sense. In addition, if the particle to be analyzed is stopped in the desired position, it is not necessary for the positioning unit 120 to generate a flow. In this case, the fluid will be at rest.

The above-described mechanism contrast with mechanisms known from the state of the art which use a fluidic trap, which operate by means of the creation of a stagnation zone and cannot be considered driving mechanisms, since the flow that positions the particle has a saddle profile, i.e. it is not one-way. In the device described with reference to FIG. 3 and explained hereinbelow in greater detail with reference to FIGS. 4 to 9, it is not necessary to maintain constant flows in the analysis chamber once the particle to be analyzed has reached the predefined position. This allows considerably reducing the quantity of positioning fluid used during the analysis. On the contrary, in devices that use fluidic traps, in order to maintain the stability of the stagnation zone it is necessary that the flows are active during the entire analysis, i.e. the device generates flows even when the particle reaches the desired position.

The analysis device 100 is suitable for analyzing cells in suspension. Said device can also be used in order to analyze cells in adhesion. In this case, in order to be able to exploit the advantages of the analysis device 100 and in particular the positioning mechanisms for the particle to be analyzed 10 by means of a positioning fluid, the cells in adhesion can be introduced in the analysis device 100 together with the medium on which they adhere. In such case, the analysis circuit 100 and in particular the positioning unit 120 can be used for controlling the position of the medium to which the cells adhere in a manner such that the cells in adhesion are, for example, centered at the focal point of an optical system. A man skilled in the art will clearly understand that in this case, the particle 10 referred to by the present invention will comprise the medium and the cells in adhesion on the medium.

In particular, according to one embodiment of the present invention the at least one detected parameter can comprise the position of the particle in the analysis chamber 110 or the position and the velocity of the particle in the analysis chamber 110. Other examples of parameters used by the analysis device 100 for the positioning of the particle to be analyzed 10 will be described hereinbelow with reference to the other figures. The analysis device according to one embodiment of the present invention can also comprise a plurality of channels 101. Said channels 101 are connected to the positioning unit 120. Said positioning unit 120 can release and/or introduce at least part of the positioning fluid from the/in the analysis chamber through at least one of the plurality of channels, so as to generate the positioning flow. The positioning flow can be generated by controlling, in a selective manner, the flow of the fluid in at least one of the plurality of channels.

Figure 4:
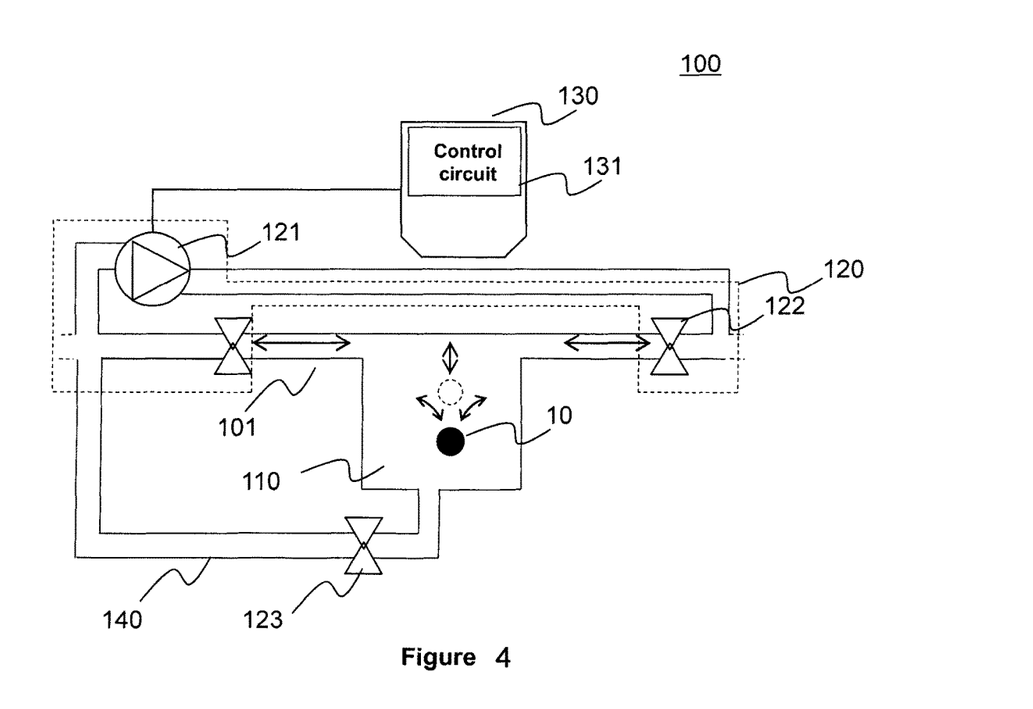
FIG. 4 is a schematic representation of a detail of an analysis device according to one embodiment of the present invention.

The operation of the analysis device 100 will be described in more detail with reference to FIG. 4. FIG. 4 is a schematic representation of a possible embodiment of the analysis device 100 described in FIG. 3. Elements already described above, with reference to FIG. 3, will not be described hereinbelow. In this embodiment of the analysis device 100, the at least one positioning unit comprises a pump 121. The pump 121 has a configuration such to allow the positioning of a particle by means of the direct action thereof of a positioning flow with sufficiently low and sufficiently controlled flow rate. For example, the pump 121 can be adapted to reverse the generated flow in less than ten seconds time. In such a manner it is possible to prevent the loss of the particle due to adhesion to the surfaces of the analysis chamber, or because it exits by means of the micro-channels connected thereto. In addition the pump 121 can be sized so as to generate linear velocities at the center of the channels less than one hundred micrometers per second. Such velocities allow retaining the particle to be analyzed inside a region of the analysis chamber, such as the focus of an optical device or any other region of interest, which has dimensions on the order of magnitude of a millimeter. The activation and deactivation of the pump 121 can be controlled by a control circuit 131, which can process the information provided by the optical device and send the control signals to the at least one positioning unit.

Even if the microfluidic systems commonly used for the analysis and the positioning of a particle can have configurations that comprise channels for injecting fluids in the analysis chamber, the geometries, sizing and technical characteristics of pumps used in such devices for the introduction/removal of the fluid are not suitable for controlling the position of a particle through the use of temporary flows as occurs in the device of FIG. 3 and of following figures, and hence such pumps are not suitable for the use described in the present invention. In particular, the pumps commonly used for microfluidic systems, such as those described above, comprise systems for the generation of stagnation points, and are not usually able to generate flows with linear velocities less than one hundred micrometers per second at the center of a channel with 10,000 square micrometer section, and are not usually able to reverse the direction of the flow in less than ten seconds time when they are delivering a flow of this flow rate.

Particular examples of pumps that can be used in the analysis device 100 will be described hereinbelow. In particular, the positioning unit 120 can be a hydrothermal pump, a peristaltic pump, a mechanical pump, or a pressure control system. In particular the analysis device 100 can comprise a network of channels 101 connected in a fluidic manner to the analysis chamber 110. During the use of the analysis device 100, the analysis chamber 110 along with the channels 101 can be filled with a positioning fluid in which a particle to be analyzed 10 can be immersed. The fluid can be a liquid, such as a culture solution for biological material or an aqueous solution. Alternatively, the fluid can be a gas, such as air or an inert gas, or a mixture of gases.

Alternatively, according to one embodiment of the present invention, the positioning unit 120 can be configured so as to generate a temporary local positioning flow in the positioning fluid consisting of convective motion due to temperature gradients generated at the walls and/or inside the analysis chamber. Such temperature gradients can for example be generated by the transfer of heat, by means of thermoelectric elements and/or by means of focused lasers. The temperature of the positioning fluid can be controlled in a manner so as to create a temperature differential between different portions of the analysis chamber 110. The temperature differential between different portions of the analysis chamber 110 signifies that the positioning fluid portions at different temperature have different mass densities. The differential of the mass density in the positioning fluid portions generates a motion of the positioning fluid in a predefined direction depending on the mass density of the positioning fluid. In one particular embodiment, the walls of an analysis chamber 110 are in direct contact with a positioning unit 120 that comprises thermoelectric elements, whose activation and deactivation is controlled by the detection and control unit 130. In an alternative embodiment, the positioning unit 120 comprises at least one laser beam focused in the analysis chamber 110. Such at least one laser beam is activated and deactivated by the detection and control unit 130, so as to generate the above-described temperature and mass density differential.

Contrary to the solutions known from the state of the art, the analysis device 100 according to the present invention allows controlling the position of the particle and hence driving the particle into a predefined position in the analysis chamber 110 by means of intermittent flows, i.e. without inducing continuous flows in the analysis chamber 110 that generate a stagnation zone. In other words, in the analysis device according to the present invention, the particle to be analyzed is driven by inducing, in the analysis chamber, aimed transient flows that act directly on the particle to be analyzed, opposing and counterbalancing a movement of the particle to be analyzed. During the positioning or in general during the analysis inside the analysis chamber 110, the use of intermittent one-way positioning flows renders superfluous the use of continuous flows in the analysis chamber and the consequent generation of a stagnation zone, or it renders superfluous the presence of other traps.

Specifically, at rest, the particle to be analyzed 10 can be randomly moved inside the analysis chamber 110 due to external factors such as gravity, convective motion of the fluid or other local flows spontaneously induced in the fluid by external perturbations. Consequently the particle 10 can be moved with respect to a predefined point in the analysis chamber 110, such as the focal center of an optical device used in order to analyze the particle 10. Such movements of the particle 10 inside the analysis chamber 110 can be corrected by inducing, in a selective manner, flows in the fluid in which the particle is immersed directly at the particle 10, as described above. The flows can be induced by selectively controlling the flow of the positioning fluid which is situated in the channels 101 connected in a fluidic manner to the analysis chamber 110. For such purpose, the positioning unit 120 is connectable to a control circuit 131, such control circuit 131 receives information on at least one parameter of the particle to be analyzed, detected by the detection and control unit 130. The at least one parameter of the particle to be analyzed can be, for example, the position of the particle to be analyzed 10 in the analysis chamber. Alternatively the at least one parameter of the particle can comprise the position and the velocity of the particle 10 or morphological, physical, biochemical or chemical characteristics thereof. In such a manner, the position of the particle 10 can be controlled in an extremely precise manner. Specifically, the control of the flow of the positioning fluid in the channels 101 on the basis of the at least one detected parameter of the particle 10 allows controlling the position of the particle in the three spatial directions in the analysis chamber 110 with a precision on the order of magnitude of 10 micrometers per second. The parameters detected by the at least one positioning unit can affect the positioning mechanism in two different ways: parameters such as morphological, physical, biochemical or chemical characteristics can be used for selecting where to move the particle, while parameters such as position and velocity can be used for determining the parameters of the particle movement mechanism.

On the basis of the at least one parameter detected by the detection and control unit 130, the positioning unit can control the flow of the positioning fluid in the network of channels 101 in order to control the position of the particle to be analyzed 10. The control of the position of the particle to be analyzed 10 can comprise the maintenance of a current position of the particle to be analyzed 10 and the movement of the particle to be analyzed 10 inside the analysis chamber 110. Specifically, if the particle to be analyzed 10 is already in the analysis position, the positioning unit 120 can be deactivated, or it can be used for maintaining the particle to be analyzed 10 in such position for the entire duration of the analysis. The analysis position could for example be the focal point of an optical apparatus. Alternatively, the positioning unit 120 can be used for moving the particle to be analyzed 10 inside the analysis chamber 110. In this manner the particle to be analyzed 10 can be positioned in a predefined position in the analysis chamber 110. The predefined position could for example be the analysis position, a position at one of the channels 101 and in particular of the channel used for introducing the particle to be analyzed 10 in the analysis chamber 110 or for extracting the particle 10 from the analysis chamber 110. In addition, the predefined position could for example be a wider region inside the analysis chamber, e.g. if the analysis of the particle includes the determination of its weight or mass density by means of the observation of the gravitational fall thereof. The man skilled in the art will however clearly understand that the control of the position of the particle to be analyzed 10 must be intended in a wide manner, for example including a movement that induces the rotation of the particle, so as to display it by means of the detection and control unit 130 from different angles and carry out, for example, a three-dimensional reconstruction thereof.

The positioning unit 120 comprises, in the embodiment of FIG. 4, at least one pump 121 and a plurality of valves 122. Each channel 101 is provided with a respective valve 122, which can be controlled so as to vary the resistance of the corresponding channel 101. In such a manner, the flow rate of the flow generated by the pump 121 can be independently and selectively controlled in each of the channels 101 so as to generate in the analysis chamber 110, at the position of the particle to be analyzed, a plurality of flows with different velocity, flow rate and direction. Specifically, through the selective control of the valves, it is possible to generate, in the analysis chamber 110, a temporary flow having a predefined direction and velocity and that acts directly on the particle 10. In this manner, a flow with non-zero velocity is generated in the suspension fluid in the analysis chamber 110 exactly in proximity to the particle to be analyzed 10 and for the time necessary for driving the particle into a predefined position. Consequently the particle to be analyzed 10 is driven in the flow with non-zero velocity generated by the positioning unit 120 and is moved in the analysis chamber in the direction along which the flow generated by the positioning unit 120 flows. Once the particle to be analyzed 10 has reached the predefined position in the analysis chamber 110, the valves can be operated in a manner so as to interrupt the flow induced on the particle to be analyzed 10. At this point, the pump 121 and the valves 122 can be operated so as to maintain the particle to be analyzed 10 in the predefined position, as described above, if the particle to be analyzed is moved from said predefined position.

The analysis device 100 also comprises a drain valve 123 through which it is possible to extract, from the analysis chamber 110, a suspension fluid and/or the particle to be analyzed 10. In one exemplifying embodiment, the drain valve 123 is connected to a drain channel 140 connected in a fluidic manner to the base of the analysis chamber 110. The drain channel 140 can also be connected to one of the channels 101. Alternatively the drain channel can be connected to a tank (not shown in the figure) containing a culture fluid or liquid. Of course, such embodiment is merely exemplifying and the man skilled in the art will clearly understand that the drain channel 140 can be connected at any other point of the analysis chamber 110.

In the device 100, each of the plurality of channels can be sized with respect to the dimensions of the analysis chamber in a manner such that an fluid change operation inside the analysis chamber at least partly occurs by means of diffusive transport.

Figure 5:
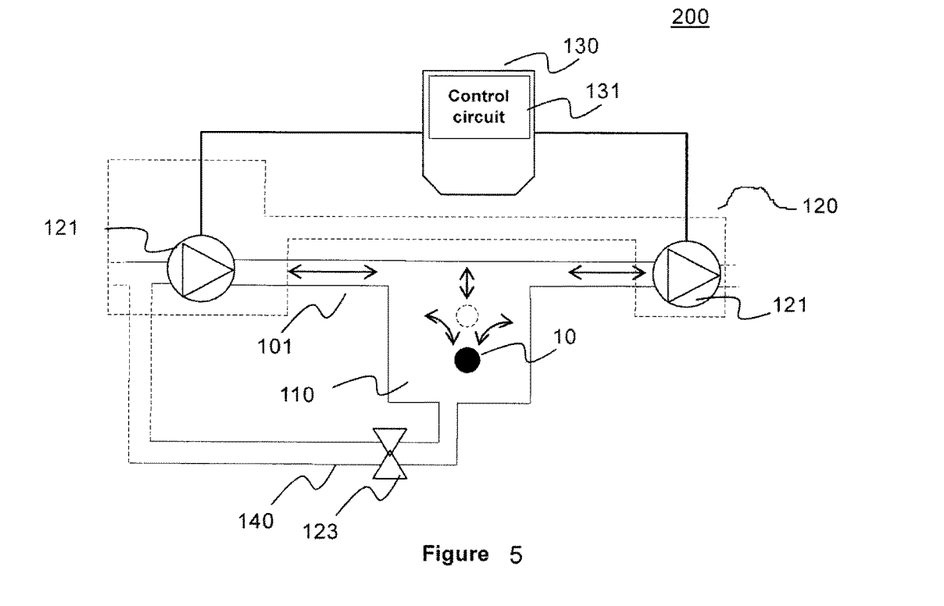
FIG. 5 is a schematic representation of a detail of an analysis device 200 according to a further development of the present invention.

FIG. 5 is a schematic representation of a detail of an analysis device 200 according to a further development of the present invention. The device is essentially similar to that described above with reference to FIG. 4 and equivalent parts will not be described hereinbelow. Unlike the device of FIG. 4, a positioning unit 120 of the analysis device 200 comprises a plurality of pumps 121, where each pump is connected to a corresponding channel 101. Such solution renders superfluous the use of the valves described in relation to FIG. 4, since the flow of fluid in each of the channels 101 can be independently and selectively controlled by means of the corresponding pump 121. A man skilled in the art will clearly understand that, even though valves 122 are superfluous in the analysis device 200, an embodiment of the device 200 comprising such valves 122 can be taken under consideration.

According to this embodiment, it is possible to control with extreme precision both the velocity and the direction of the single flows generated in the analysis chamber 110. Specifically, the detection and control unit 130 is adapted to detect one or more properties of the particle to be analyzed 10, such as those already described in relation to the preceding figures, including, for example, the current position of the particle 10, its velocity and drift direction of the particle 10. On the basis of such detected properties of the particle 10, a control circuit 131 determines, for each of the channels 101 in fluidic connection with the analysis chamber 110, the flow rate and the direction of the flow necessary for controlling the position of the particle 10. The properties of the particle to be analyzed 10 can be detected by an optical system composed for example by a standard phase contrast microscope objective, a condenser lens, a filter composed of a phase ring, and an illumination system for white light microscopy or for fluorescent microscopy. The image thus generated can be recorded by an optical sensor and processed by a computer or by a microcontroller. In addition, an illumination of the analysis chamber can be activated or deactivated by a commercial shutter.

The flow rate and the direction of the flow in each of the channels 101 could, for example, be determined on the basis of a three-dimensional value of the predefined position in the analysis chamber 110 and of a three-dimensional value of the current position of the particle to be analyzed. The three-dimensional value of the predefined position can be a value inserted by the user by means of an input/output interface (not shown in the figure) connectable to the control circuit 131 or in general to the analysis device 200. Alternatively, the three-dimensional value of the predefined position could be a preset value. For example, a preset value of the predefined position could be the focal point of the optics included in or connectable to the analysis device 200. In addition to the values of the predefined position and of the current position of the particle 10, the control circuit 131 could also determine the flow rate of the flows in the channels 101 on the basis of the velocity of the particle to be analyzed and of a drift direction thereof. Of course, the man skilled in the art will clearly understand that other parameters of the particle to be analyzed 10 can be taken under consideration in order to determine the flow rate and the direction of the flows in the channels 101 used for controlling the position of the particle 10. The detection and control unit 130 and the control circuit 131 described with reference to the device of FIG. 4 and following figures can also be used in the device described with reference to FIG. 3.

The pumps 121 could for example be peristaltic pumps, syringe pumps and the like. Advantageously the positioning unit 120 can comprise at least one hydrothermal pump controlled through a thermoelectric element or by means of irradiation of electromagnetic waves, e.g. in the infrared spectrum. The exemplifying embodiment of the case of control by means of hydrothermal pump controlled through a thermoelectric element will be better discussed hereinbelow. It is clear from the description that based on one aspect of the invention which uses pumps connected to the control circuit 131, such as that described by FIG. 5, the temporary positioning flow is generated outside the analysis chamber 110, thus preventing the positioning unit from generating stress on the particles under analysis, and in particular on the cells. It is clear that this advantage would not exist if the temporary positioning flow is generated inside the analysis chamber, or if the temporary positioning flow is generated by applying force fields that cross inside the analysis chamber.

Figure 6:
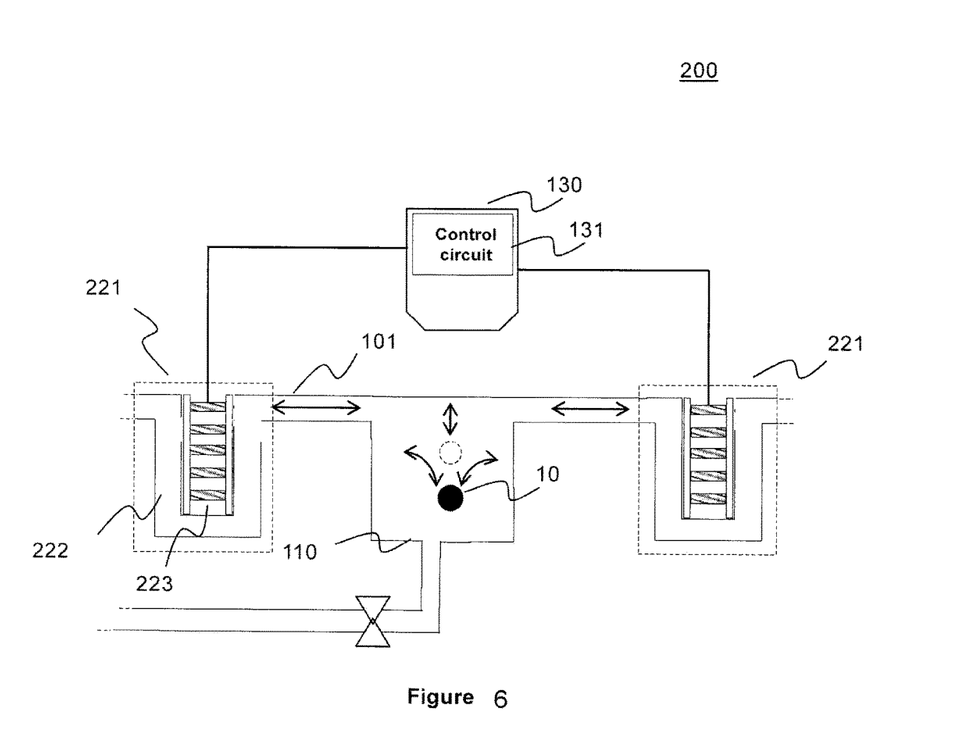
FIG. 6 shows a detail of the analysis device according to an alternative embodiment.

FIG. 6 schematically shows a analysis device 200 that uses hydrothermal pumps connected to the control circuit 131. In this embodiment, each channel 101 is connected to a hydrothermal pump 221 through which it is possible to precisely control the flow rate and the direction of the flow of the positioning fluid. The hydrothermal pump 221 comprises at least one channel 222 containing the positioning fluid. The channel 222 containing the positioning fluid can for example be a portion of the channel 101. The temperature of the positioning fluid inside the channel 222 can be externally controlled so as to create a temperature differential between different portions of the channel 222. The temperature differential between different portions of the channel 222 signifies that the portions of positioning fluid in the sections of the channel 222 at different temperature have different mass densities. The differential of the mass density in the portions of positioning fluid generates a motion of the positioning fluid in a predefined direction dependent on the mass density of the positioning fluid. In one particular embodiment of the hydrothermal pump 221, the geometry of the channel comprises at least two vertically arranged sections, connected to each other by at least one horizontally arranged section. In the following discussion, the term vertical is used to indicate a direction perpendicular to the plane of the base of the analysis chamber 110, while the term horizontal defines a direction parallel to the plane of the base of the analysis chamber. In such embodiment, the temperature of the positioning fluid in the channel 222 can be controlled in a manner such that the temperature in a first vertical section of the channel 222 is greater than the temperature in a second vertical section of the channel 222. Such control of the temperature generates a mass density difference of the positioning fluid in the vertical sections of the channel, thus inducing a motion of the positioning fluid. Clearly, by reversing the control of the temperature such that the temperature of the positioning fluid in the first vertical section of the channel 222 is lower than the temperature of the positioning fluid in the second vertical section of the channel 222, it is possible to reverse the direction of the flow of the positioning fluid. The geometry of the channel 222 described in the preceding paragraph is merely exemplifying and the man skilled in the art will clearly understand that any solution that allows inducing a mass density difference of the positioning fluid in at least one section of the channel 101 falls within the idea of the present invention. For example, the geometry of the channel used for the hydrothermal pump 221 can comprise at least two horizontally arranged sections.

The control of the temperature in the channel 222 can, according to one particular embodiment of the device 200, be carried out by means of a heat pump 223 or a thermoelectric element, such as a Peltier cell. The heat pump is connected to the control circuit 131 and operated by the control circuit 131 so as to generate the desired positioning flow. In particular, the heat pump 223 can include a first surface in thermal connection with the first vertical section of the channel 222 and a second surface in thermal connection with the second vertical section of the channel 222. The first and the second surface can be separated by a core that maintains the temperature difference, e.g. by means of an electronic circuit. In the examples reported in FIG. 6 and in the following FIG. 7, the first vertical section of the channel 222 is the channel part that directly faces the analysis chamber 110 and the first surface of the heat pump is the surface thermally connected to said first vertical section of the channel, while the second vertical section of the channel 222 is the channel part further away from the analysis chamber 110. The second surface of the heat pump is in this case the surface thermally connected to said second vertical section of the channel 222.

Alternatively, resistors can be placed in direct contact with the first and second vertical section of the channel 222, respectively. The resistors can be selectively operated on the basis of the values of flow rate and direction of the flow determined by the control circuit 131 so as to induce the temperature difference and hence the mass density difference of the positioning fluid in the first and second vertical section of the channel 222, so as to generate the requested flow of the positioning fluid.

Alternatively the control of the temperature in the channel 222 can, according to a particular embodiment of the device 200 according to the present invention, be carried out by means of a series of thermistors, such as a series of PT100 thermistors, i.e. platinum thermistors in which the resistance at 0° C. is equal to 100 ohm. The series of thermistors is connected to the control circuit 131 and operated by the control circuit 131 so as to generate the desired positioning flow. In particular, according to one embodiment of the present invention, such thermistors can be used for generating the heat necessary for the temperature, and simultaneously they can be used for measuring the temperature, so as to prevent undesired effects such as overheating, which can lead for example to the boiling of the positioning fluid. In particular, the use of said thermistors offer another two operating advantages, in addition to the temperature measurement: 1) said thermistors are commercial components generally produced only for measuring temperature and hence they are optimized for the exchange of heat, even in small-size regions, comparable to the size of the channels 222. On the contrary, the other commercial resistors optimized for heat exchange on flat surfaces, such as the side of a channel 222, normally have overly-large size with respect to said channels 222. 2) The cost of said commercial thermistors is an order of magnitude lower than the cost of Peltier cells which have size comparable to the channels 222.

In general, it is also clear from the description that based on one aspect of the invention which uses hydrothermal pumps connected to the control circuit 131, like that described in FIG. 6, the temporary positioning flow is generated without mechanical or electrical elements coming into direct contact with the positioning fluid.

Figure 7A:
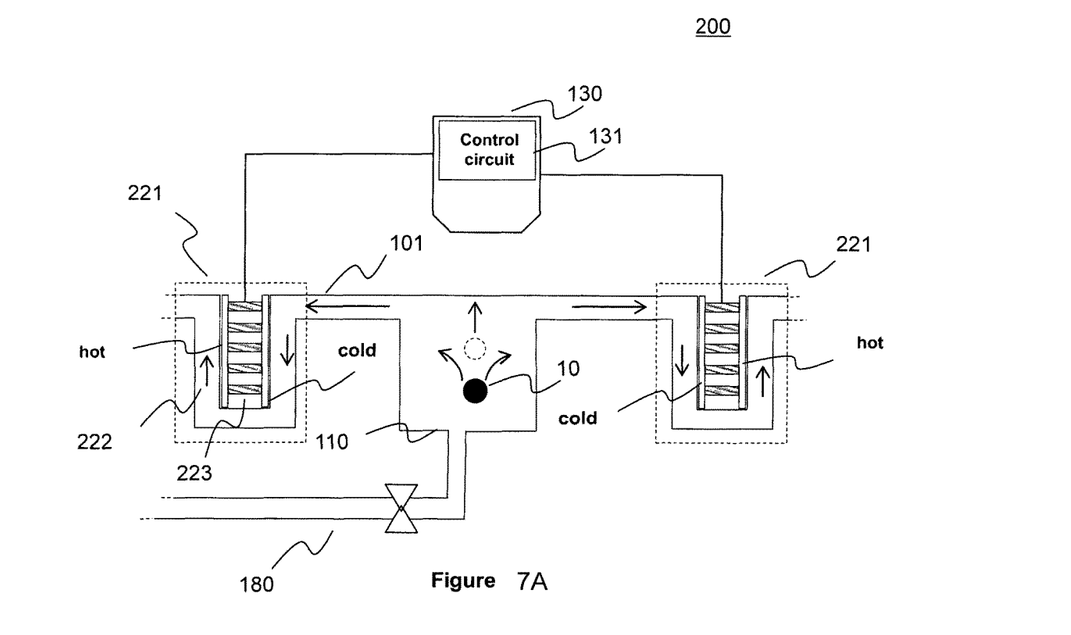
FIGS. 7A and 7B are schematic illustrations which show the analysis device in operation.

FIG. 7A shows the analysis device 200 in operation. For description simplicity, the analysis device 200 illustrated in FIG. 7A comprises two channels 101 connected in a fluidic manner to the analysis chamber 110. It is in any case understood that the analysis device according to the present invention can comprise more than two channels. Specifically, the higher the number of channels 101, the more precise the control of the position and/or the positioning itself of the particle to be analyzed 10.

FIG. 7A shows the analysis device 200 while it is operated to move the particle to be analyzed 10 in a vertical direction from a base of the analysis chamber 110 towards the upper end of the analysis chamber 110. In this context, by vertical direction it is intended a direction perpendicular to the base of the analysis chamber 110. In order to obtain such movement along the vertical, a plurality of flows is generated in the analysis chamber that all have the same flow rate and which flow from the interior of the analysis chamber 110 towards the positioning channels 101. In order to obtain this, in each of the channels 101—on the basis of the data calculated by the control circuit 131 as described above with reference to FIG. 5—a flow is generated that flows inside the channel 101 in a direction that goes from the point at which the channel 101 is introduced in the analysis chamber 110 towards an opposite end of the channel. In each of the channels, the flow rate of the flow thus generated is such that the resulting positioning flow, at the point of the analysis chamber where the particle 10 is situated, flows along a direction perpendicular to the base of the analysis chamber. In order to generate one such flow, the control circuit 131 operates the heat pump 223 such that the second surface in thermal connection with the second vertical section of the channel 222 is at a greater temperature than the temperature of the first surface in thermal connection with the first vertical section of the channel 222. In such a manner, the mass density of the fluid portion in the second vertical section of the channel 222 is lower than the mass density of the fluid portion in the first vertical section of the channel 222, thus causing a movement of the fluid from the first vertical section of the channel towards the second vertical section of the channel 222. The variation of the mass density of the fluid portion in each channel is proportional to the flow rate of the flow that one wishes to generate in such channel.

By controlling, by means of the control circuit 131, the flows in the positioning fluid in each of the channels 101 such that they have the same flow rate, and that the first surface in thermal connection with the first vertical section of the channel 222 is at a greater temperature than the temperature of the second surface in thermal connection with the second vertical section of the channel 222, an overall flow will act on the particle to be analyzed 10 that is symmetrical with respect to an axis of the particle 10 perpendicular to the base of the analysis chamber and which is directed towards the base of the analysis chamber 110. Such overall flow will oppose the Archimede's thrust to which the particle 10 is subjected and will cause a movement of the particle 10 in a vertical direction towards the base of the analysis chamber.

Analogously, in order to generate a flow in the channel 101 that flows from the end of the channel 101 towards the analysis chamber 110, the heat pump 223 is controlled in a manner such that the first surface in thermal connection with the first vertical section of the channel 222 is at a greater temperature than the temperature of the second surface of the heat pump 223.

Figure 7B:
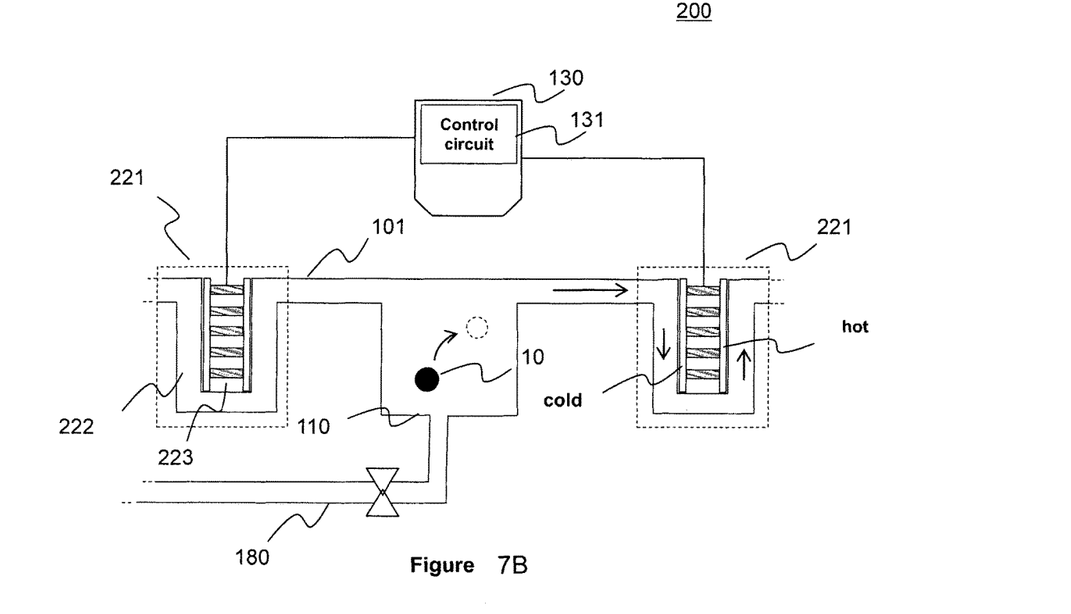

FIG. 7B shows the analysis device 200 operated in a manner so as to move the particle 10 laterally in the analysis chamber 110. The control circuit 131 can control the heat pumps such to create a positioning flow only in one of the channels 101. Specifically, the control circuit 131 can induce a temperature differential between the surfaces of only one of the heat pumps 223, and leave the surfaces of the remaining heat pump at the same temperature. In this manner, in the channel 101 connected to the heat pump 223 having the surfaces at the same temperature, the positioning fluid will be at rest. Alternatively the heat pumps in each of the channels 101 can be operated so as to make the positioning fluid flow into each of the channels 101 in a single sense.

In addition, if for example the particle 10 must be moved in a direction parallel to the base of the analysis chamber, the control circuit 131 can control the heat pumps 223 so as to generate a positioning flow in one of the channels 101 so as to cause a lateral movement of the particle 10 and a positioning flow with smaller flow rate, possibly intermittent, in the remaining channel 101 having the function of correcting the position of the particle 10 in a manner such that the latter is essentially moved along a direction parallel to the base of the analysis chamber 110. The man skilled in the art will clearly be able to understand that the correction of the position of the particle 10 will be more precise with a higher number of channels 101 and respective heat pumps used for generating the positioning flows.

In addition, the analysis device 200 can be operated in a manner such that the movement of the particle 10 occurs along a predefined path, also for reaching a predefined position in the analysis chamber 110 according to predefined times. In one development of the present invention, the control circuit 131 can control the activation of the hydrothermal pumps by using a standard feedback system of PID type, based on proportional, integral and derivative information obtained from the relative position of the particle with respect to the desired position.

In general, the man skilled in the art will clearly understand that a movement of the particle 10 along a direction that is not parallel to a direction perpendicular or parallel to the base of the analysis chamber 110 can be obtained by selectively generating, in each of the channels 101, position control flows having different flow rate and, possibly, senses. In this manner it is possible to adjust, in an extremely precise manner, the direction, sense and intensity of the resulting force acting on the particle to be analyzed 10.

The analysis device 100, 200 according to the present invention may further comprise a temperature and pH regulation circuit adapted to regulate the temperature and the pH of the positioning fluid in the analysis chamber.

Figure 8:
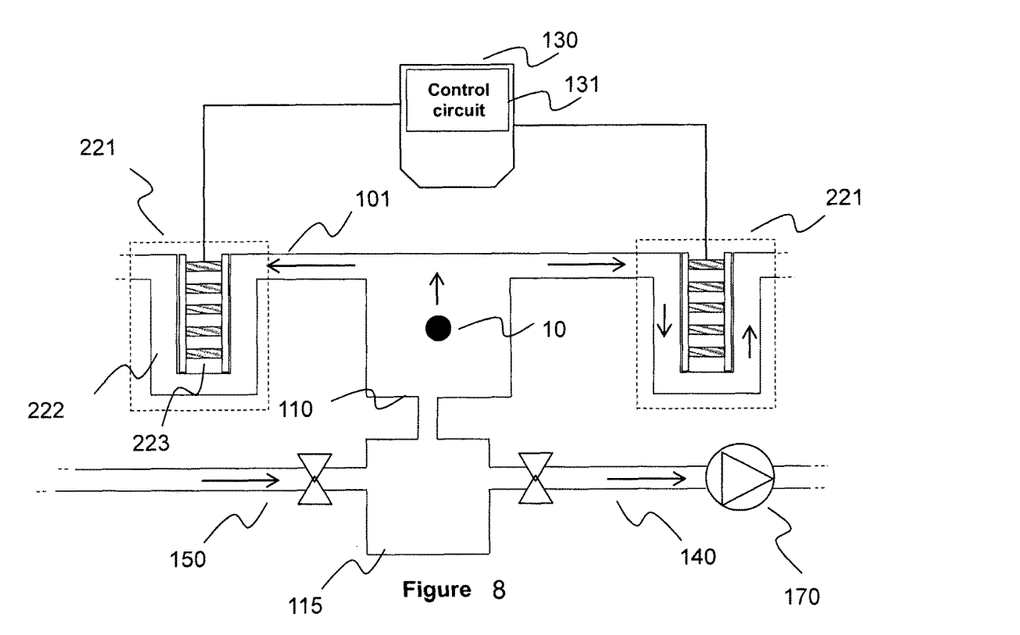
FIG. 8 is a schematic illustration that shows a further development of the analysis device in operation in which the change of fluid in the analysis chamber occurs by means of diffusive transport.

FIG. 8 shows a further implementation of the analysis device 200 operated so as to allow a fluid change operation inside the analysis chamber 110 at least in part by means of diffusive transport. As already described above, in the analysis device according to the present invention, the channels 101 are sized with respect to the size of the analysis chamber in a manner such that the fluid change operation inside the analysis chamber at least partly occurs by means of diffusive transport.

Specifically, in this embodiment, a fluid change chamber 115 is connected to the analysis chamber, to a drain channel 140 and to an injection channel 150 and a drain pump 170, e.g. a syringe pump, is connected to the drain channel 140. A flow induced by the drain pump 170 into the drain channel 140 can generate a flow between the injection channel 150 and the drain channel 140, which can substitute the fluid contained in the fluid change chamber 115 without directly invading the analysis chamber 110. The diffusion of the fluids between the fluid change chamber 115 and the analysis chamber 110 will make the contents of the chambers uniform, with a single fluid of equivalent composition. In this embodiment, the ratio between the volume of the fluid change chamber 115 and the volume of the analysis chamber 110 is greater than 50. In such a manner, the final fluid, following the diffusive transport, has a composition substantially equivalent to the injected fluid. In addition, the ratio between the overall hydrodynamic resistance of the network of channels 101 and the hydrodynamic resistance of the network composed of the drain channel 140 and the injection channel 150 is at least greater than 10, in a manner such that the particle is not affected by flows induced in the analysis chamber by the fluid change operation.

Even if in the analysis devices 100, 200 illustrated in FIGS. 3 to 8, the analysis chamber 110 is incorporated in the analysis device and connected in a fixed manner to the positioning unit and to the channels 101, the analysis chamber 110 can alternatively be configured as a removable part of the analysis device. According to such embodiment, the analysis chamber can be a disposable element, to be substituted each time the analysis on the particle contained therein has concluded. In this embodiment, in the analysis device 100, 200, the analysis chamber is comprised in a disposable chip, where said disposable chip can comprise an analysis chamber in order to analyze the particles in suspension and/or an analysis chamber in order to analyze particles in adhesion. Consequently, different analysis types can be conducted with the same device through the substitution of a single element, suitable configured so to be removable, with a considerable reduction of costs.

Figure 9:
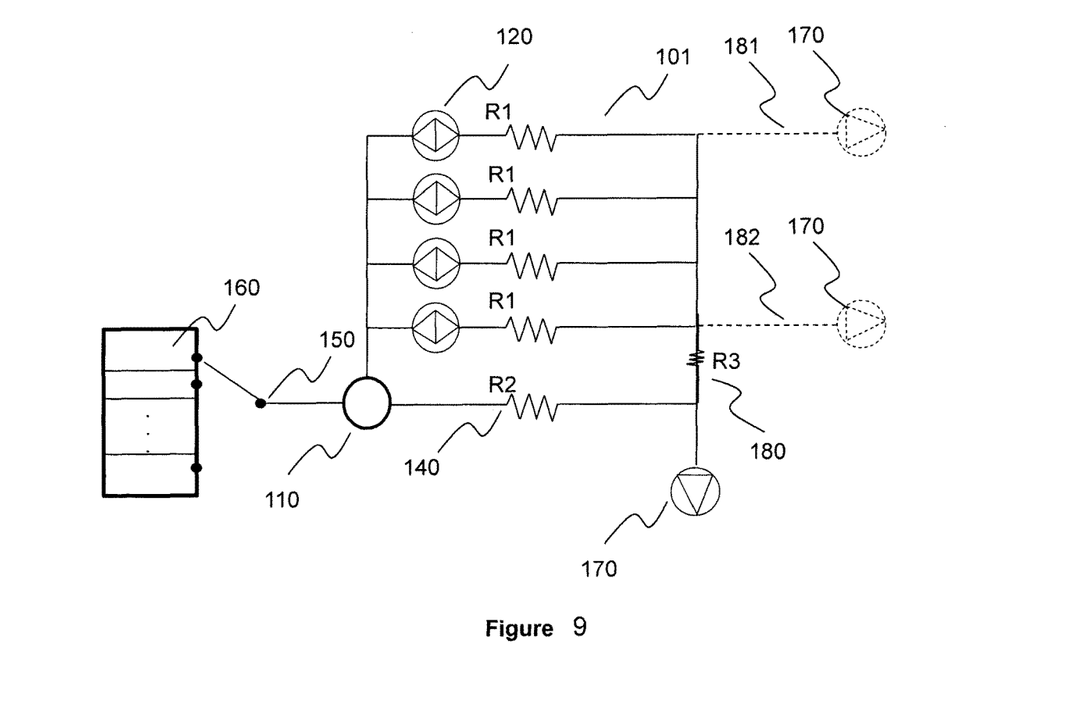
FIG. 9 shows a fluidic circuit diagram of a portion of the analysis device according to the present invention.

FIG. 9 shows a fluidic circuit diagram of the analysis device 100, 200 according to the present invention. The analysis chamber 110 is schematically represented in FIG. 9 as a circumference. Clearly, such representation is merely exemplifying and non-limiting of the actual shape and configuration of the analysis chamber 110. According to the present invention, the analysis chamber 110 is connected to at least one channel 101 for the positioning of the particle 10 and to at least one positioning unit 120, arranged as in one of the FIGS. 3 to 8.

The circuit diagram illustrated in FIG. 9 represents, in particular, an embodiment that implements an analysis device as illustrated in FIGS. 3 to 8. The man skilled in the art will however clearly understand that other circuit representations corresponding to alternative embodiments of the analysis device, such as the embodiment illustrated in FIG. 4, are possible in the scope of and without departing from the object of the present invention.

The analysis chamber 110 can also be connected to at least one injection channel 150, from which the positioning fluid and the particle to be analyzed 10 can be introduced in the analysis chamber 110 and in the channels 101. The injection channel 150 can be connected to a further fluidic device 160, such as a valve system, a system for selecting different fluids, or a device for selecting the particle under analysis. The analysis chamber 110 can also be connected to at least one drain channel 140 for the removal of the positioning fluid. For the purpose of maintaining the fluidic system balanced, the channels 101, 140 and 150 can be connected to other points of the network of channels by means of vent channels 180. Specifically, FIG. 9 shows a fluidic circuit diagram where the injection channel 150 is only connected to a fluid selection system 160, while the drain channel 140 is collectively connected to the positioning channels 101 and to a drain pump 170. In the representation in FIG. 9, the drain pump 170 is used for the operations of changing the positioning fluid in the analysis chamber and for the operation preliminary to instrument use that provides for the filling of the fluidic network composed of the elements 101, 110, 120, 140, 150, 180 with fluid, where the network of channels is sized so as to allow the filling of all the elements of the network.

One possible embodiment of the network of channels provides for the use of channels having different fluid-dynamic resistances. In this context, the fluid-dynamic resistance in the various circuit branches (channels) can be varied by varying the length and/or the diameter of the channels themselves. Specifically, with reference to the circuit of FIG. 9, the resistance of the various channels constituting the network of the analysis device can be selected so as to respect the following relation $$R1/4 > R3 >> R2.$$

For a configuration of the network of channels like that described in FIG. 9, the equivalent fluid-dynamic resistance R1 of the system of channels 101, connected in parallel, must be greater than the fluid-dynamic resistance R3 of the vent channel 180, which must be much greater than the fluid-dynamic resistance R2 of the drain channel 140. With the term much greater, it is intended a resistance that is at least one order of magnitude greater. The man skilled in the art will however clearly understand that the above-described relation, valid for the network of channels schematically illustrated in the circuit diagram of FIG. 10, can vary if the analysis device 100, 200 is implemented using a network of channels different from that shown in FIG. 9.

Even if the analysis device described in FIGS. 3 to 8 shows only two channels 101 containing positioning fluid, it must be clear that the invention is not limited to such embodiment and that the embodiments of FIGS. 13 to 8 were illustrated as comprising two channels 101 only for the sake of description simplicity. It is in any case understood that the analysis devices 100, 200 described in relation to the figures from 3 to 8 can comprise more than two channels 101, as for example illustrated in the circuit diagram of FIG. 9, without departing from the object of the present invention.

Optionally, the analysis device 100, 200 according to the present invention could comprise an initialization channel in fluidic connection with one of the channels 101. In the circuit diagram of FIG. 9, such initialization channel 181 could be represented by a circuit branch connected to one of the branches 101. The initialization channel 181 can in turn be connected to a drain pump 170, e.g. a syringe pump, by means of which fluid can be introduced inside the circuit.

Similarly, in addition or alternatively, the circuit described in FIG. 9 can also include an injection channel 182 through which a particle to be analyzed, such as a cell, can be introduced in the circuit of channels of the analysis device 100, 200. As already described above, with regard to the initialization and drain channels 181 and 140, also the injection channel can be connected to a drain pump 170, e.g. a syringe pump. It is in any case understood that the initialization channels 181 and injection channels 182, represented in FIG. 9 in fluidic connection with one of the channels 101, can be alternatively fluidically connected to other regions of the microfluidic network if a network of channels is used that is different from that shown in FIG. 9, without departing from the object of the present invention. For example, such initialization channels 181 and injection channels 182 can be connected to the analysis chamber 110 and/or to the injection channel 150.

The present invention also refers to a method for analyzing a particle, in particular biological material, such as cells and the like. Said method can comprise one or more steps as described in each of the FIGS. 3 to 9.

In particular, the method comprises the introduction of the particle to be analyzed in an analysis chamber containing a positioning fluid. One parameter of the particle in the analysis chamber, where the particle to be analyzed is in suspension in the positioning fluid, is then detected, for example through the detection and control unit described above. The method also comprises, during a particle analysis operation, the generation of a temporary positioning flow in the positioning fluid through the activation of at least one positioning unit, where said temporary positioning flow acts directly on the particle and drives the particle into a predefined position in the analysis chamber. During a particle analysis operation, when the particle to be analyzed is in the predefined position, the at least one positioning unit can be deactivated such that the positioning fluid is at rest.

In this manner, the position of the particle to be analyzed can be controlled through the generation, in the positioning fluid, of a positioning flow that acts directly at the particle to be analyzed. The positioning flow in the analysis chamber 110 is temporary, in the sense that it can be generated and interrupted during the analysis of the particle based on the position of the particle in the analysis chamber 110, as will be explained hereinbelow. Since the presence of constant flows in the analysis chamber 110 is not necessary for controlling the position of the particle to be analyzed, the method described herein therefore allows reducing the quantity of fluid necessary for completing an analysis, thus reducing the complexity and the costs of use of the device itself.

The positioning flow is generated on the basis of the at least one detected parameter of the particle to be analyzed.

Figure 10:
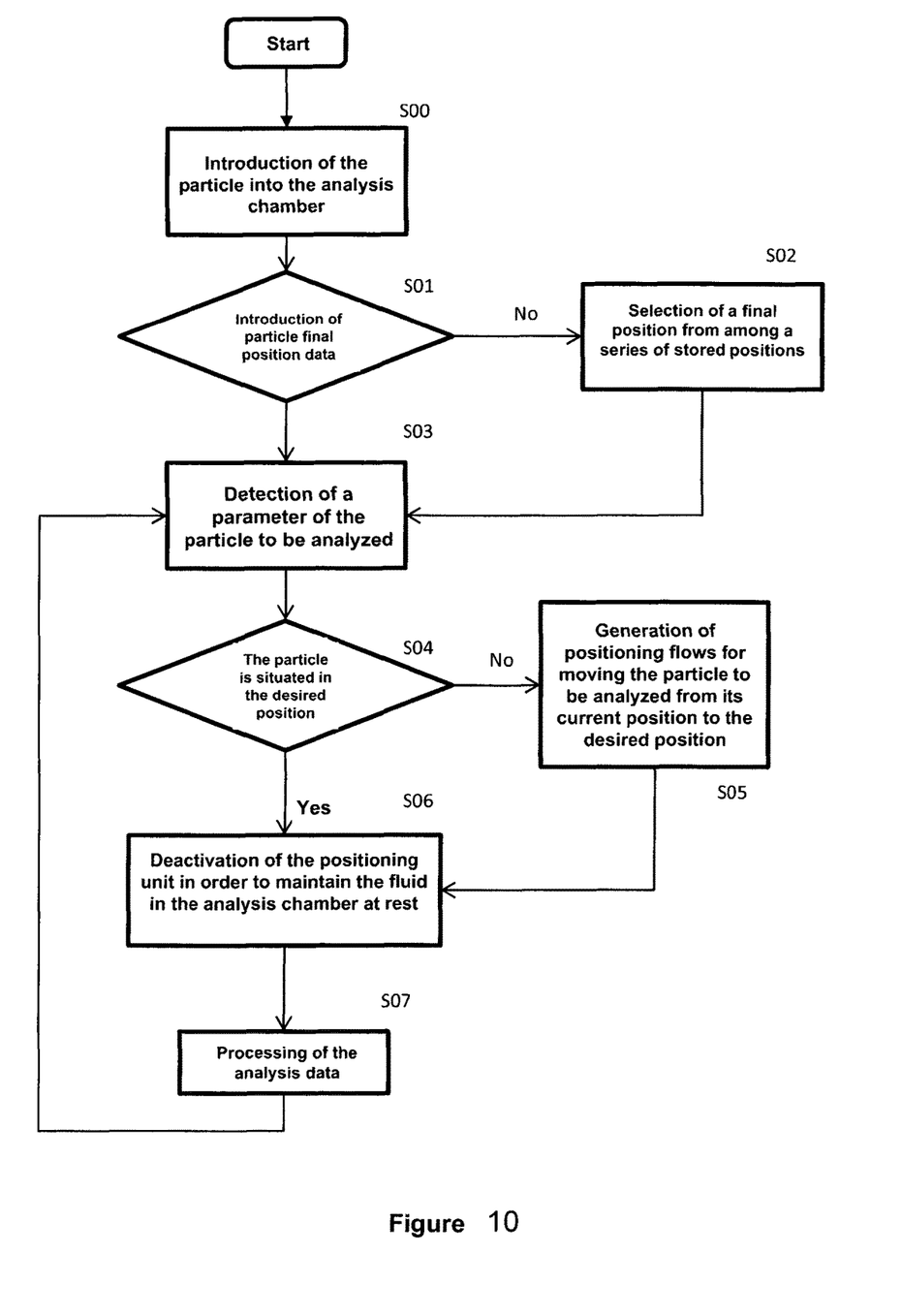
FIG. 10 is a flow diagram that illustrates a method for analyzing a particle in an analysis chamber according to the present invention.

FIG. 10 is a flow diagram that illustrates a method for analyzing a particle in an analysis chamber 110 according to one embodiment of the present invention. The method for analyzing the particle 10 comprises the step of introducing the particle to be analyzed 10 in an analysis chamber 110 containing a positioning fluid (step S00). In step S01, the analysis device 100, 200, can require the user to introduce data relative to the desired final position of the particle to be analyzed. Such step is optional. If the data relative to the desired final position of the particle is not introduced by the user, the analysis device 100, 200 selects, in step S02, a value corresponding to a desired final position from among a series of position values stored in a memory of the control circuit 131. The desired final position can, for example, be selected based on the type of analysis to be carried out on the particle 10. The desired final position could, for example, be the focal point of an objective of an analysis instrument, a point on the trajectory of a laser beam, a zone of the analysis chamber 110 at an extraction channel for the analysis device or the like. Once the final position is selected, the method passes to step S03. If the value of the final position of the particle is directly inserted by the user, the method passes directly from step S01 to step S03.

In step S03, the control circuit 131 detects at least one parameter of the particle in the analysis chamber, where the particle to be analyzed is in suspension in the positioning fluid. In some embodiments, the invention can be referred to a method, where the detection of the parameter of the particle also comprises the detection of the position of the particle or of the position and velocity of the particle to be analyzed in the positioning fluid. Specifically, the at least one parameter of the particle to be analyzed can for example comprise a current position of the particle 10, a value of the current velocity of the particle 10 and/or its drift direction. Clearly, based on requirements and on the type of analysis and positioning required, the parameter of the particle to be analyzed may only include one of the abovementioned parameters or other parameters, such as the size of the particle, its density and its weight. In general, each parameter that could affect or condition the movement of the particle can be taken under consideration.

In step S04, the analysis device determines if the particle is already situated in the desired final position, such as the focal point of an objective or a light beam. If the particle is situated in the desired position, the method passes to step S06 in which the analysis device deactivates the positioning unit in order to maintain the fluid in the analysis chamber at rest.

If, in step S04, it is established that the particle is not found in the desired position, the analysis circuit operates in step S05 the positioning unit 120 as described above with reference to FIGS. 3 to 9, so as to move the particle to be analyzed from its current position to the desired final position. In this case, the positioning flows are adjusted so as to counterbalance even the random motion of the particle 10 caused by external agents. After this, the method passes to step S06, described above.

During the particle movement step, the positioning flow is generated on the basis of the at least one detected parameter of the particle to be analyzed. In particular, the positioning flow is used in the analysis device according to one embodiment of the present invention for directly opposing a movement of the particle to be analyzed. Such movement could be a random movement of the particle to be analyzed 10 due to perturbations or external forces, such as gravity, convective motion, or the like or a movement of the particle 10 previously induced through positioning flows. Consequently, in the analysis chamber 110, one or more positioning flows are present that are generated by the positioning unit 120, which act directly on the particle 10, without creating stagnation zones inside the analysis chamber where the particle to be analyzed is trapped. In addition, in the analysis chamber 110, it is possible to deactivate the positioning flows when the particle is situated in the predefined position.

In other words, contrary to analysis devices known from the state of the art, in the analysis chamber 110 a flow gradient is not created for trapping a particle at the minimum flow point, but rather the particle is driven by using the positioning flows. Consequently and contrary to devices known from the state of the art, during an operation of positioning the particle 10, the velocity of the positioning flow at the particle to be analyzed is non-zero: the particle is driven through the analysis chamber 110 by means of the positioning flow. In addition, contrary to analysis devices known from the state of the art, it is not necessary to generate continuous flows that generate a trap for the particle, rather the particle is driven by flows generated as required, which can be deactivated, avoiding the waste of costly fluids, and allowing the attainment of a fluidically static situation in the analysis chamber.

Finally, in step S07, the analysis device 100, 200 proceeds with the analysis of the particle 10. In particular, the analysis device processes the analysis data. Such analysis can be executed according to the forms and methods known from the state of the art.

As already explained above with reference to FIGS. 3 to 9, also in the method according to the present invention the control of the position of the particle by means of the positioning flow can be achieved through the selective control of one or more flows in one or more channels connected to the analysis chamber. In particular, during the selective control of the flows, at least part of the positioning liquid can be injected or expelled from the analysis chamber.

It was also shown that, based on one aspect of the present invention, the temporary positioning flow is generated without mechanical or electrical elements coming into direct contact with the positioning fluid.

Even though different embodiments have been described with reference to FIGS. 3 to 9 and with reference to the method of FIG. 10, the man skilled in the art will clearly understand that these can be combined, if possible, in particular even by selecting only some characteristics of different exemplifying embodiments and combining them together.

What is claimed is:

1. A device controlling
a particle used for analyzing the particle comprising:
an analysis chamber, wherein said analysis chamber contains the particle suspended in a fluid;
a plurality of fluid channels, each coupled to said analysis chamber, wherein controlled flow of the fluid is configured to control movement of the particle in three dimensions in the fluid;
a detector configured to detect at least one parameter of the particle suspended in the fluid in the analysis chamber;
a plurality of pumps one of said plurality of pumps coupled to one of said plurality of fluid channels, each of said plurality of pumps comprising a unit configured to be activated and deactivated on the basis of the detected at least one parameter of the particle, wherein said plurality of pumps control fluid flow within said plurality of fluid channels; and
a control unit configured to activate at least one of said plurality of pumps so as to generate a temporary positioning flow in any spatial direction in the three-dimensional space in the fluid, wherein the temporary positioning flow acts directly on the particle and drives the particle into a predefined position in said analysis chamber without use of a trap for the particle;
wherein said control unit is further configured to deactivate at least one of said plurality of pumps when the particle is in the predefined position such that the fluid in the analysis chamber is at zero velocity, and
wherein the particle is configured to being moved to the predefined position and held without continuous fluid flow and stagnation points or zones are not generated in said analysis chamber.

2. The device according to claim 1,
wherein during driving of the particle into the predefined position, said detector activates at least one of said plurality of pumps in a manner such that a local flow at a position of the particle is non-zero.

3. The device according to claim 1, wherein driving of the particle into the predefined position occurs in a direct manner by friction that acts between the temporary positioning flow and the particle.

4. The device according to claim 1, wherein positioning of the particle is only controlled by the temporary positioning flow and when the fluid is at rest, no flows are present in the analysis chamber.

5. The device according to claim 1,
wherein the at least one parameter comprises a position of the particle in said analysis chamber or a position and velocity of the particle in said analysis chamber.

6. The device according to claim 1,
wherein said plurality of pumps are configured for generating independently and in a selective manner, in each channel of said plurality of fluid channels, position control flows having different velocity, flow rate, and direction.

7. The device according to claim 1, wherein said plurality of pumps are connected in a fluidic manner to said analysis chamber, such that the temporary positioning flow is generated outside the analysis chamber.

8. The device according to claim 1, wherein each of said plurality of fluid channels is sized with respect to a size of said analysis chamber in a manner such that a fluid change operation inside said analysis chamber at least partly occurs by diffusive transport.

9. The device according to claim 1, wherein the temporary positioning flow is generated without mechanical or electrical elements coming into direct contact with the fluid.

10. The device according to claim 1, wherein the at least one of said plurality of pumps is a hydrothermal pump comprising a thermoelectric element.

11. The device according to claim 1,
wherein said analysis chamber is comprised in a disposable chip, wherein said analysis chamber comprised in the disposable chip is configured to analyze particles in suspension or adhesion.

12. A method for analyzing a particle, the method comprising the steps of:
introducing the particle into an analysis chamber containing a positioning fluid;
detecting a parameter of the particle in the analysis chamber, wherein the particle is in suspension in the positioning fluid;
generating, during an analysis of the particle, a temporary positioning flow in any spatial direction in three-dimensional space in the positioning fluid through activation of at least one positioning unit, wherein the temporary positioning flow acts directly on the particle and drives the particle into a predefined position in the analysis chamber without use of a trap for the particle; and deactivating, during the analysis of the particle, the at least one positioning unit when the particle is in the predefined position such that the positioning fluid in the analysis chamber is at rest.

13. The method according to claim 12, wherein flows configured to generate stagnation points or zones are not generated in the analysis chamber nor are they generated in the positioning fluid.

14. The method according to claim 12, wherein during driving of the particle into the predefined position, a local flow at a position of the particle is non-zero.

15. The method according to claim 12, wherein the particle is driven into the predefined position by friction that acts directly between the positioning fluid and the particle.

16. The method according to claim 12, wherein positioning of the particle is only controlled by the temporary positioning flow and when the positioning fluid is at rest, no flows are present in the analysis chamber.

17. The method according to claim 12, wherein said step of detecting the parameter of the particle comprises detection of a position of the particle or of a position and a velocity of the particle in the positioning fluid.

18. The method according to claim 12, wherein control of a position of the particle by the temporary positioning flow is attained through independent and selective control of a velocity, flow rate and sense of a plurality of flows in a plurality of channels connected to the analysis chamber.

19. The method according to claim 12, wherein the temporary positioning flow is generated outside the analysis chamber.

20. The method according to claim 12, wherein the temporary positioning flow is generated without mechanical or electrical elements coming into direct contact with the positioning fluid.

21. The method according to claim 12, wherein: said step of generating the temporary positioning flow results from convection motion due to a temperature differential between different portions of the positioning fluid.

22. A method for analyzing a particle, the method comprising the steps of:

providing the device of claim 1, introducing the particle into said analysis chamber containing the fluid;

detecting the at least one parameter of the particle in said analysis chamber, wherein the particle is in suspension in the fluid;

generating, during an analysis of the particle, the temporary positioning flow in any spatial direction in the three-dimensional space in the fluid through the activation of at least one of said plurality of pumps, wherein the temporary positioning flow acts directly on the particle and drives the particle into a predetermined position in said analysis chamber; and deactivating, during the analysis of the particle, at least one of said plurality of pumps when the particle is in the predefined position such that the fluid in the analysis chamber is at rest.

* * * * *